United States Patent [19]
Ho

[11] Patent Number: 6,099,540
[45] Date of Patent: Aug. 8, 2000

[54] TONGUE SCRAPER

[76] Inventor: Vu H. Ho, 1520 Rainforest, West Covina, Calif. 91790

[21] Appl. No.: 09/321,156

[22] Filed: May 27, 1999

[51] Int. Cl.[7] .................................................. A61B 17/24
[52] U.S. Cl. ............................................................ 606/161
[58] Field of Search .................................... 606/161, 166, 606/162, 131; 493/141; 132/308, 309; 15/111, 143.1, 167.1

[56] References Cited

U.S. PATENT DOCUMENTS

| | | | |
|---|---|---|---|
| 2,218,072 | 10/1940 | Runnels | 606/161 |
| 2,583,750 | 1/1952 | Runnels | 606/161 |
| 5,810,856 | 9/1998 | Tveras | 606/161 |
| 5,868,769 | 2/1999 | Rosenblood et al. | 606/161 |

*Primary Examiner*—Michael Buiz
*Assistant Examiner*—Jackie Tan-Uyen T. Ho

[57] ABSTRACT

A tongue scraper for scrapping residue and debris off of a user's tongue. The tongue scraper includes a scraping body having a pair of opposite elongate end portions, and an arcuate middle portion interposed between the end portions of the scraping body. The arcuate middle portion of the scraping body has concave and convex edges and a pair of substantially flat faces. The faces of the arcuate middle portion each have therein a plurality of spaced apart residue grooves.

12 Claims, 2 Drawing Sheets

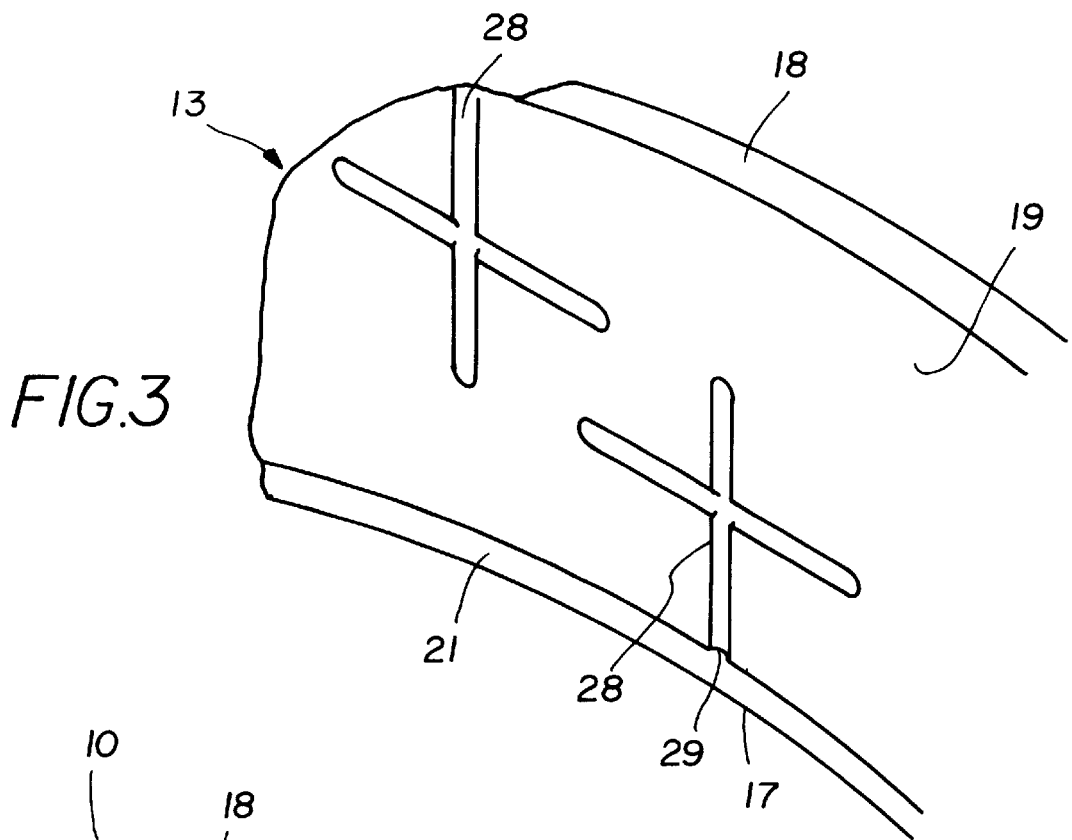
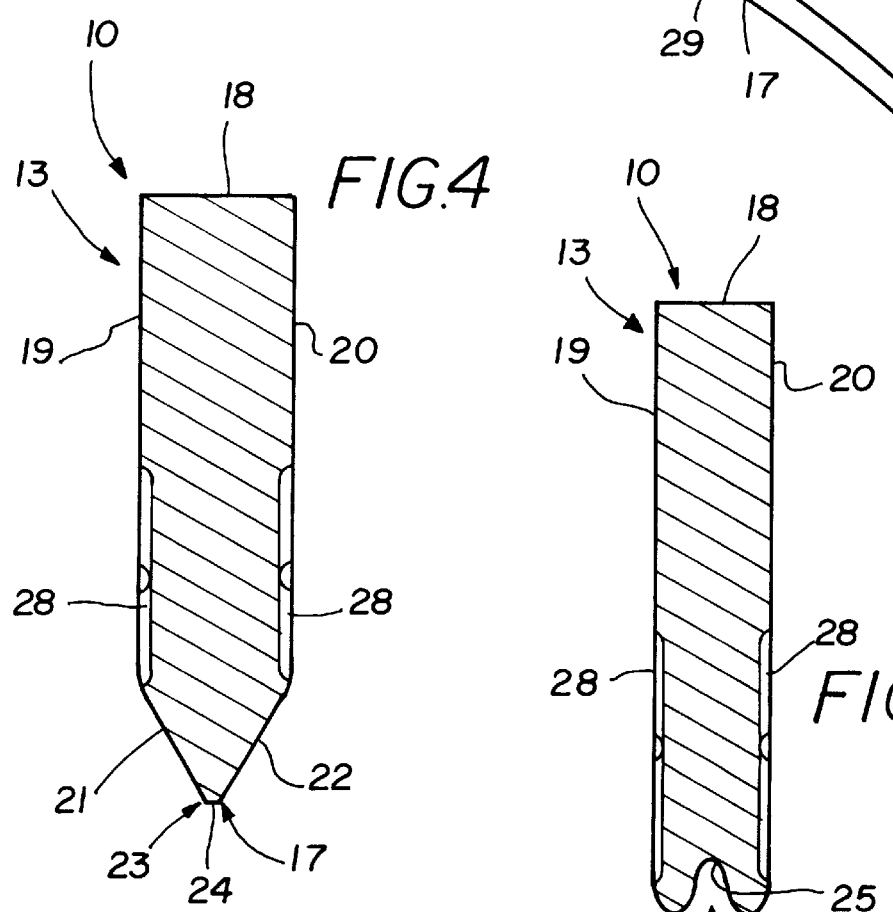

TONGUE SCRAPER

BACKGROUND OF THE INVENTION

1. Field of the Invention

The present invention relates to tongue scrapers and more particularly pertains to a new tongue scraper for scrapping residue and debris off of a user's tongue.

2. Description of the Prior Art

The use of tongue scrapers is known in the prior art. More specifically, tongue scrapers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 1,893,524; U.S. Pat. No. 3,683,924; U.S. Pat. No. Des. 361,618; U.S. Pat. No. 5,061,272; U.S. Pat. No. 4,875,496; and U.S. Pat. No. 1,533,123.

While these devices fulfill their respective, particular objectives and requirements, the aforementioned patents do not disclose a new tongue scraper. The inventive device includes a scraping body having a pair of opposite elongate end portions, and an arcuate middle portion interposed between the end portions of the scraping body. The arcuate middle portion of the scraping body has concave and convex edges and a pair of substantially flat faces. The faces of the arcuate middle portion each have therein a plurality of spaced apart residue grooves.

In these respects, the tongue scraper according to the present invention substantially departs from the conventional concepts and designs of the prior art, and in so doing provides an apparatus primarily developed for the purpose of scrapping residue and debris off of a user's tongue.

SUMMARY OF THE INVENTION

In view of the foregoing disadvantages inherent in the known types of tongue scrapers now present in the prior art, the present invention provides a new tongue scraper construction wherein the same can be utilized for scrapping residue and debris off of a user's tongue.

The general purpose of the present invention, which will be described subsequently in greater detail, is to provide a new tongue scraper apparatus and method which has many of the advantages of the tongue scrapers mentioned heretofore and many novel features that result in a new tongue scraper which is not anticipated, rendered obvious, suggested, or even implied by any of the prior art tongue scrapers, either alone or in any combination thereof.

To attain this, the present invention generally comprises a scraping body having a pair of opposite elongate end portions, and an arcuate middle portion interposed between the end portions of the scraping body. The arcuate middle portion of the scraping body has concave and convex edges and a pair of substantially flat faces. The faces of the arcuate middle portion each have therein a plurality of spaced apart residue grooves.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tongue scraper apparatus and method which has many of the advantages of the tongue scrapers mentioned heretofore and many novel features that result in a new tongue scraper which is not anticipated, rendered obvious, suggested, or even implied by any of the prior art tongue scrapers, either alone or in any combination thereof.

It is another object of the present invention to provide a new tongue scraper which may be easily and efficiently manufactured and marketed.

It is a further object of the present invention to provide a new tongue scraper which is of a durable and reliable construction.

An even further object of the present invention is to provide a new tongue scraper which is susceptible of a low cost of manufacture with regard to both materials and labor, and which accordingly is then susceptible of low prices of sale to the consuming public, thereby making such tongue scraper economically available to the buying public.

Still yet another object of the present invention is to provide a new tongue scraper which provides in the apparatuses and methods of the prior art some of the advantages thereof, while simultaneously overcoming some of the disadvantages normally associated therewith.

Still another object of the present invention is to provide a new tongue scraper for scrapping residue and debris off of a user's tongue.

Yet another object of the present invention is to provide a new tongue scraper which includes a scraping body having a pair of opposite elongate end portions, and an arcuate middle portion interposed between the end portions of the scraping body. The arcuate middle portion of the scraping body has concave and convex edges and a pair of substantially flat faces. The faces of the arcuate middle portion each have therein a plurality of spaced apart residue grooves.

Still yet another object of the present invention is to provide a new tongue scraper that helps maintain oral hygiene and fresh breath.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic enlarged perspective view taken from circle 3 of FIG. 2 illustrating the residue grooves.

FIG. 4 is a schematic cross sectional view of an embodiment of the present invention taken from line 4—4 of FIG. 1.

FIG. 5 is a schematic cross sectional view of another embodiment of the present invention taken from line 5—5 of FIG. 2.

DESCRIPTION OF THE PREFERRED EMBODIMENT

With reference now to the drawings, and in particular to FIGS. 1 through 5 thereof, a new tongue scraper embodying the principles and concepts of the present invention will be described.

As best illustrated in FIGS. 1 through 5, the tongue scraper generally comprises a scraping body having a pair of opposite elongate end portions, and an arcuate middle portion interposed between the end portions of the scraping body. The arcuate middle portion of the scraping body has concave and convex edges and a pair of substantially flat faces. The faces of the arcuate middle portion each have therein a plurality of spaced apart residue grooves.

In closer detail, the tongue scraper includes a scraping body 10 having a pair of opposite elongate end portions 11,12, and an arcuate middle portion 13 interposed between the end portions of the scraping body. In one embodiment, the scraping body may comprise a resilient metal material such as a resilient stainless steel material.

In one preferred embodiment, the end portions of the scraping body may be substantially collinear with one another. In such in embodiment, the end portions and the middle portion of the scraping body may also lie in a common plane with one another.

Figure 1:
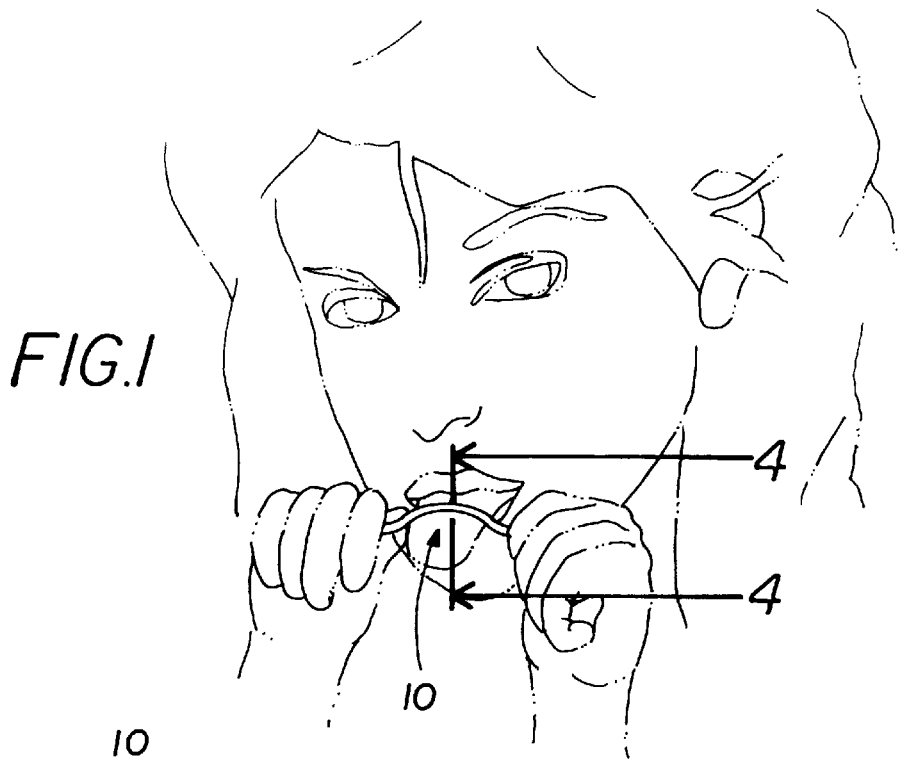
FIG. 1 is a schematic perspective view of a new tongue scraper in use according to the present invention.
Figure 2:
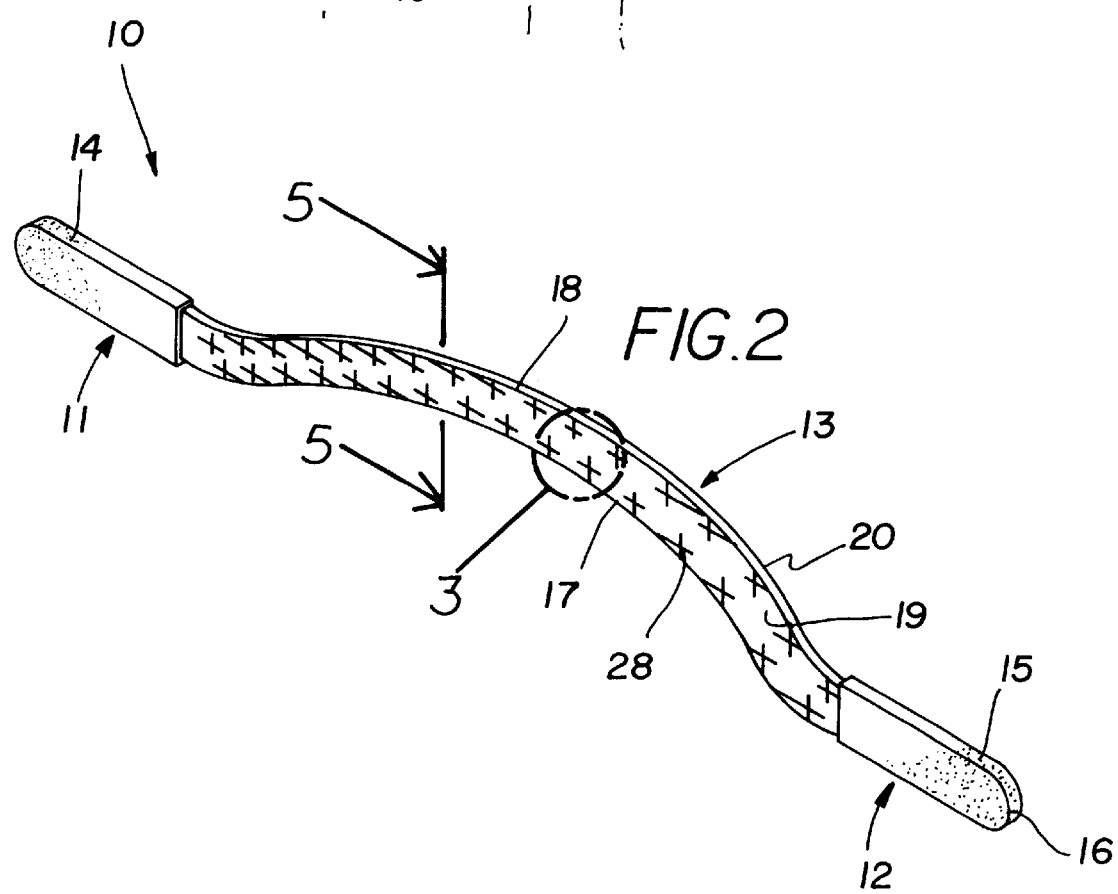
FIG. 2 is a schematic perspective view of the present invention.

The end portions of the scraping body are designed for grasping with the user's fingers as illustrated in FIG. 1. A pair of sheaths 14,15 may be provided. One of the sheaths receives one of the end portions of the scraping body therein and the other of the sheaths receives the other of the end portions of the scraping body therein. This way, the end portions of the scraping body are substantially covered by the sheaths.

The sheaths each may comprise a resiliently deformable material such as a resiliently deformable plastic or rubber material. In use, the sheaths are designed for frictionally enhancing the grip of the user grasping the end portions of the scraping body and also for protecting the fingers and hands of the user from injury from the end portions of the scraping body. In a preferred embodiment, each of the sheaths may have a rounded outer end 16 for further protecting the fingers and hands of the user from injury from the end portions of the scraping body.

The arcuate middle portion of the scraping body has concave and convex edges 17,18 and a pair of substantially flat faces 19,20. The concave edge of the arcuate middle portion faces towards the common line in which the end portions of the scraping body lie.

With particular reference to FIG. 4, in one embodiment of the tongue scraper, the faces of the arcuate middle portion may have portions 21,22 converging towards one another adjacent the concave edge of the arcuate middle portion such that the concave edge of the arcuate middle portion forms a single tapered scraping edge 23 designed for scraping residue and debris off of a user's tongue. The single tapered scraping edge of the arcuate middle portion preferably may have a flattened tip 24 to prevent a user from cutting their tongue on the single tapered scraping edge.

In another embodiment of the tongue scraper, the concave edge of the arcuate middle portion may have a longitudinal channel 25 extending therealong. The longitudinal channel of the concave edge defines a pair of rounded scraping edges 26,27 along the concave edge designed for scraping residue and debris off of a user's tongue. The rounded scraping edges are rounded to prevent a user from cutting their tongue on the single tapered scraping edge. In use, the longitudinal channel is designed for receiving debris and residue scraped off of the user's tongue by the rounded scraping edges.

The faces of the arcuate middle portion each have therein a plurality of spaced apart residue grooves 28. In use, each of the residue grooves is designed for receiving debris and residue scraped off of the user's tongue concave edge. With reference to FIG. 3, in one preferred embodiment, the residue grooves may each be generally cross-shaped and have a pair of elongate portions extending substantially perpendicular to one another. The cross shape is helpful in holding the scraped off debris and residue in the residue grooves.

In a preferred embodiment, at least one of the residue grooves of each face of the arcuate scraping edge has an open end 29 adjacent the concave edge of the arcuate middle portion for helping scraped off debris and residue flow into the residue groove.

In an illustrative embodiment, the scraping body may have a length defined between the end portions of about 7½ inches and a thickness defined between the faces of the arcuate middle portion of about ¼ inch for providing an optimal size for scraping most human tongues.

In use, the user grasps the end portions with their hands and scrapes debris and residue off of their tongue with the scraping edges of the concave edge of the arcuate middle portion. The debris and residue that is scraped off the user's tongue is accumulated in the longitudinal channel of the pair of rounded scraping edge embodiment and in the residue grooves where it may then be rinsed off of the scraping body with water.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tongue scraper, comprising:

a scraping body having a pair of opposite elongate end portions, and an arcuate middle portion interposed between said end portions of said scraping body;

said arcuate middle portion of said scraping body having concave and convex edges and a pair of substantially flat faces; and said faces of said arcuate middle portion each having therein a plurality of spaced apart residue grooves.

2. The tongue scraper of claim 1, wherein said end portions of said scraping body are substantial collinear with one another.

3. The tongue scraper of claim 1, further comprising a pair of sheaths, one of said sheaths receiving one of said end portions of said scraping body therein and the other of said sheaths receiving the other of said end portions of said scraping body therein.

4. The tongue scraper of claim 3, wherein said sheaths each comprise a resiliently deformable material.

5. The tongue scraper of claim 3, wherein each of said sheaths has a rounded outer end.

6. The tongue scraper of claim 1, wherein said faces of said arcuate middle portion have portions converging towards one another adjacent said concave edge of said arcuate middle portion such that said concave edge of said arcuate middle portion forms a single tapered scraping edge.

7. The tongue scraper of claim 6, wherein said single tapered scraping edge of said arcuate middle portion has a flattened tip.

8. The tongue scraper of claim 1, wherein said concave edge of said arcuate middle portion has a longitudinal channel extending therealong, said longitudinal channel of said concave edge defining a pair of rounded scraping edges along said concave edge.

9. The tongue scraper of claim 1, wherein said residue grooves each are generally cross-shaped.

10. A tongue scraper, comprising:

a scraping body having a pair of opposite elongate end portions, and an arcuate middle portion interposed between said end portions of said scraping body;

said end portions of said scraping body being substantially collinear with one another;

a pair of sheaths, one of said sheaths receiving one of said end portions of said scraping body therein and the other of said sheaths receiving the other of said end portions of said scraping body therein such that said end portions of said scraping body are substantially covered by said sheaths;

said sheaths each comprising a resiliently deformable material;

each of said sheaths having a rounded outer end;

said arcuate middle portion of said scraping body having concave and convex edges and a pair of substantially flat faces;

said faces of said arcuate middle portion having therein a plurality of spaced apart residue grooves; and wherein said residue grooves each are generally cross-shaped.

11. The tongue scraper of claim 10, wherein said faces of said arcuate middle portion have portions converging towards one another adjacent said concave edge of said arcuate middle portion such that said concave edge of said arcuate middle portion forms a single tapered scraping edge, wherein said single tapered scraping edge of said arcuate middle portion has a flattened tip.

12. The tongue scraper of claim 10, wherein said concave edge of said arcuate middle portion has a longitudinal channel extending therealong, said longitudinal channel of said concave edge defining a pair of rounded scraping edges along said concave edge.

* * * * *